United States Patent
Hou et al.

(10) Patent No.: US 12,264,353 B2
(45) Date of Patent: Apr. 1, 2025

(54) METHOD FOR CYCLIC BIOCHEMICAL CONVERSION OF CARBON DIOXIDE AND HOT GAS COGENERATION IN DEPLETED OIL AND GAS RESERVOIR

(71) Applicants: Southwest petroleum university, Sichuan (CN); Zhengzhou University, Henan (CN)

(72) Inventors: Zhengmeng Hou, Henan (CN); Lin Wu, Sichuan (CN); Liangchao Huang, Henan (CN); Zhifeng Luo, Sichuan (CN); Jianhua Liu, Henan (CN); Ming Dou, Henan (CN); Xuning Wu, Sichuan (CN); Qianjun Chen, Sichuan (CN); Cong Lu, Sichuan (CN)

(73) Assignees: Southwest petroleum university, Chengdu (CN); Zhengzhou University, Zhengzhou (CN)

( * ) Notice: Subject to any disclaimer, the term of this patent is extended or adjusted under 35 U.S.C. 154(b) by 0 days.

(21) Appl. No.: 18/433,433

(22) Filed: Feb. 6, 2024

(65) Prior Publication Data

US 2024/0247288 A1 Jul. 25, 2024

(30) Foreign Application Priority Data

Dec. 20, 2022 (CN) .......................... 202211654346.4
Mar. 10, 2023 (CN) .......................... 202310229522.8

(51) Int. Cl.
| | | |
|---|---|---|
| *C12P 39/00* | (2006.01) | |
| *C09K 8/582* | (2006.01) | |
| *C09K 8/594* | (2006.01) | |
| *C12P 5/02* | (2006.01) | |
| *E21B 41/00* | (2006.01) | |

(52) U.S. Cl.
CPC .............. *C12P 5/023* (2013.01); *C09K 8/582* (2013.01); *C09K 8/594* (2013.01); *E21B 41/0064* (2013.01); *Y02E 50/30* (2013.01)

(58) Field of Classification Search
CPC .......... Y02E 60/36; C12P 5/023; C12P 39/00; E21B 43/16; C12N 1/26; C10L 3/08; C10L 3/104; C10L 2290/26; C10L 2290/542
USPC ......................................................... 435/167
See application file for complete search history.

(56) References Cited

FOREIGN PATENT DOCUMENTS

| | | |
|---|---|---|
| CN | 103562340 | 2/2014 |
| CN | 114165281 | 3/2022 |
| CN | 115094094 | 9/2022 |
| JP | 2010022957 | 2/2010 |

OTHER PUBLICATIONS

"Office Action of China Counterpart Application", issued on Aug. 19, 16, 2023, with English translation thereof, pp. 1-23.
Liehui Zhang et al., "Thoughts on the development of CO2-EGR under the background of carbon peak and carbon neutrality", Natural Gas Industry B , vol. 10, Aug. 2023, pp. 383-392.

*Primary Examiner* — Robert B Mondesi
*Assistant Examiner* — Mohammad Y Meah

(57) ABSTRACT

A method for cyclic biochemical conversion of carbon dioxide and hot gas cogeneration in depleted oil and gas reservoirs includes: S1: selecting a target depleted oil and gas reservoir; S2: adjusting a temperature of the target depleted oil and gas reservoir to 30° C. to 70° C. and detecting whether formation water of the target depleted oil and gas reservoir contains methanogenic archaea, in which if no methanogenic archaeon is contained, then methanogenic archaea is injected and step S3 is proceeded, and if methanogenic archaea are contained, then step S3 is proceeded directly; S3: injecting a mixture of carbon dioxide and hydrogen into the target depleted oil and gas reservoir through a gas injection well; and S4: shutting down the gas injection well to wait for the methanogenic archaea to convert carbon dioxide and hydrogen into methane and exploiting the methane and heat energy in the target depleted oil and gas reservoir.

7 Claims, 1 Drawing Sheet

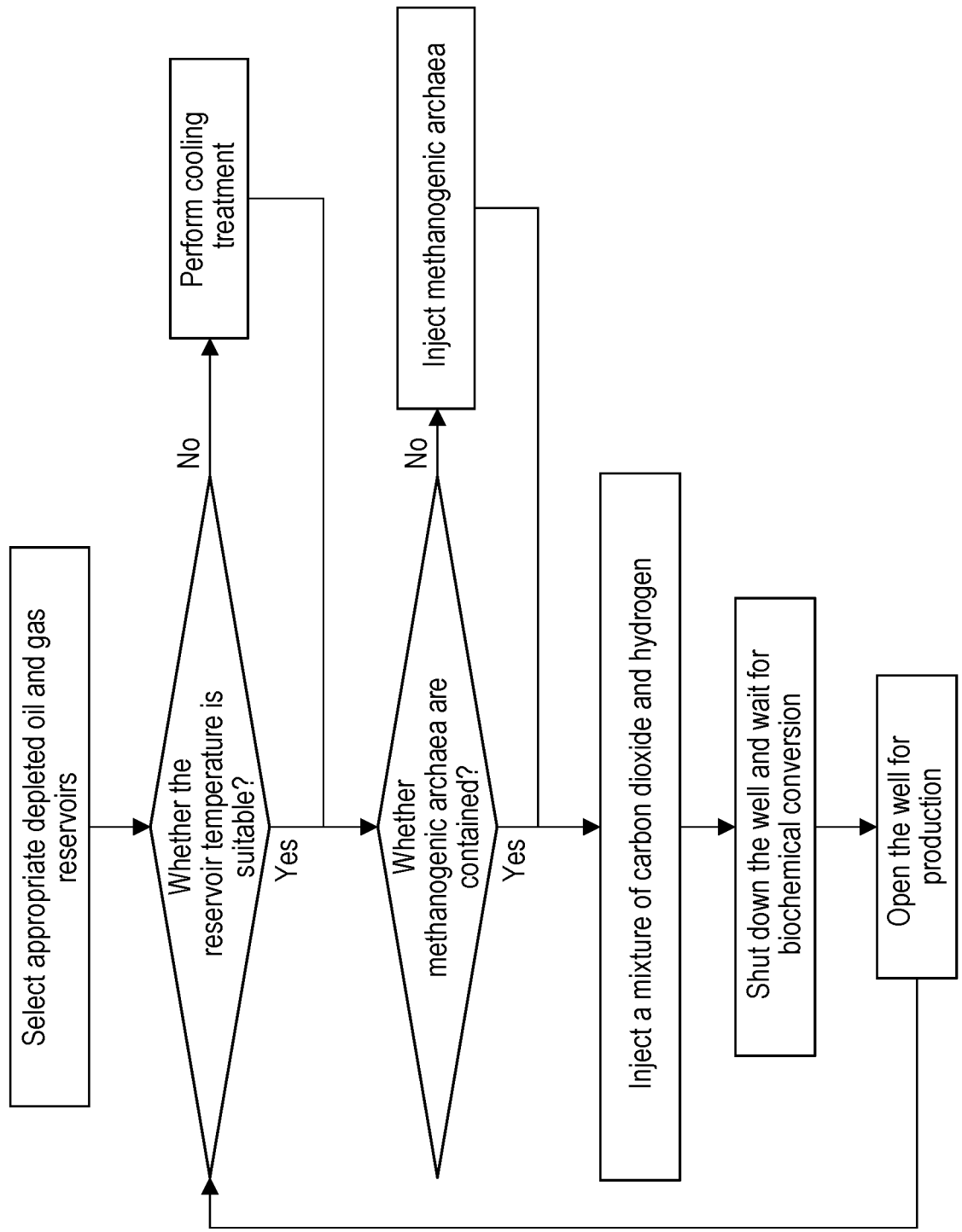

METHOD FOR CYCLIC BIOCHEMICAL CONVERSION OF CARBON DIOXIDE AND HOT GAS COGENERATION IN DEPLETED OIL AND GAS RESERVOIR

CROSS-REFERENCE TO RELATED APPLICATION

This application claims the priority benefit of China application serial no. 202310229522.8, filed on Mar. 10, 2023, which claims the priority benefit of China application serial no. 202211654346.4, filed on Dec. 20, 2022. The entirety of the above-mentioned patent applications are hereby incorporated by reference herein and made a part of this specification.

BACKGROUND

Technical Field

The disclosure belongs to the technical field of oil and gas field development, and specifically relates to a method for cyclic biochemical conversion of carbon dioxide and hot gas cogeneration in a depleted oil and gas reservoirs.

Description of Related Art

In 2016, 176 parties around the world signed the Paris Agreement, and the long-term goal thereof is to control the increase in global average temperature to less than 2° C. compared with the pre-industrial period, and strive to limit the increase in temperature to less than 1.5° C. to deal with global warming due to greenhouse effect. To achieve this goal, various countries have successively introduced carbon peaking and carbon neutrality strategies. As a member of the parties, China also proposed in September 2020 to strive that carbon dioxide emission peak before 2030 and strive to achieve the goal of carbon neutrality before 2060.

If China is to achieve the dual carbon goals, it is crucial to develop a carbon circular economy. Currently, CCUS (carbon capture, utilization, and storage) is considered the core technology in the carbon circular economy, which mainly includes, for example, carbon dioxide oil flooding, carbon dioxide enhanced gas production, carbon dioxide fracturing, carbon dioxide enhanced geothermal systems. Compared with conventional CCS (carbon capture and storage) technology, CCUS can recycle carbon dioxide resources and put into circular use to generate economic benefits, which is practical. However, the existing CCUS technology still lacks in terms of carbon recycling and economy. Therefore, it is necessary to find an economical and effective way of recycling carbon dioxide.

SUMMARY

In view of the problems and deficiencies existing in the related art, the purpose of the disclosure is to provide a method for cyclic biochemical conversion of carbon dioxide and hot gas cogeneration in depleted oil and gas reservoirs.

In order to achieve the purpose of the disclosure, the technical solutions adopted by the disclosure are as follows.

A method for cyclic biochemical conversion of carbon dioxide and hot gas cogeneration in depleted oil and gas reservoirs includes the following steps.

S1: depleted oil and gas reservoirs suitable for biochemical conversion of carbon dioxide are selected as target depleted oil and gas reservoirs.

S2: the temperature of the target depleted oil and gas reservoir is adjusted to 30° C. to 70° C. and whether the formation water of the target depleted oil and gas reservoir contains methanogenic archaea is detected. If the target depleted oil and gas reservoir does not contain methanogenic archaea, then methanogenic archaea are injected into the target depleted oil and gas reservoir and then step S3 is performed. If the target depleted oil and gas reservoir contains methanogenic archaea, then step S3 is directly proceeded.

S3: a mixture of carbon dioxide and hydrogen is injected into the target depleted oil and gas reservoir through a gas injection well.

S4: the gas injection well is shut down to wait for the methanogenic archaea to convert the carbon dioxide and hydrogen in the target depleted oil and gas reservoir into methane, and the methane and heat energy in the target depleted oil and gas reservoir are exploited.

According to the above method, further, the structure of the target depleted oil and gas reservoir described in step S1 is an anticline or a fault, the porosity is greater than 10%, the permeability is greater than 10 mD, the water saturation is greater than 10%, and the mineralization of the formation water is less than 150 g/L with the pH value being in a range of 6.4 to 7.5.

According to the method, further, the specific method for adjusting the temperature of the target depleted oil and gas reservoir to 30° C. to 70° C. in step S2 is as follows. If the temperature of the target depleted oil and gas reservoir is higher than 70° C., then pre-fluid is injected into the target depleted oil and gas reservoir to reduce the temperature of the target depleted oil and gas reservoir to 30° C. to 70° C.

According to the method, further, the pre-fluid is fresh water of 5° C. to 20° C.

According to the method, further, the methanogenic archaea described in step S2 is one or more of methanobacteriaceae, *Methanothermus stetter*, *Methanococcus kluyer* and vam niel, methanogenus, and *Methanoplanus wildgruber*.

According to the method, further, the method for detecting methanogenic archaea in step S2 is to adopt any one of enrichment culture, in situ culture, or co-culture method.

According to the method, further, the criterion for not containing methanogenic archaea described in step S2 is that the content of methanogenic archaea is less than $1\times10^{-4}$ g/L. If the content of methanogenic archaea is greater than or equal to $1\times10^{-4}$ g/L, then the target depleted oil and gas reservoir contains methanogenic archaea.

According to the method, further, the gas injection pressure of the gas injection well in step S3 needs to satisfy that the bottom hole pressure is lower than the fracture pressure of the reservoir rock.

According to the method, further, the volume ratio of carbon dioxide to hydrogen in step S3 is 3:13 to 3:12.

According to the method, further, the carbon dioxide described in step S3 is $CO_2$ captured from industrial waste gas, the atmosphere, or a mixture of industrial waste gas and the atmosphere, and hydrogen is one or more of hydrogen produced by electrolysis of water, hydrogen produced from fossil energy, and hydrogen produced from industrial by-products.

According to the method, further, the time for shutting down the gas injection well described in step S4 is half a year to one year.

According to the method, further, in step S4, carbon dioxide and hydrogen are converted into methane and heat is released under the action of methanogenic archaea, and the thermal reaction equation is as follows.

According to the method, further, the methane and heat energy exploited in step S4 are directly exported to users and/or are exported to users after power generation.

Compared with the related art, the beneficial effects of the disclosure are as follows.

(1) This disclosure captures and transports $CO_2$ in the atmosphere or industrial waste gas to the target depleted oil and gas reservoir and finally convert into methane under the action of methanogenic archaea. After being used by factories or users, methane generates $CO_2$ and is emitted into the atmosphere to be captured, thereby realizing carbon recycling, which is beneficial to develop a carbon circular economy.

(2) In the process of cyclic biochemical conversion of carbon dioxide, the disclosure rationally exploits the geothermal energy of depleted oil and gas reservoirs and the heat energy generated by microbial reproduction, which is beneficial to improving the economy of the technology.

(3) In addition to burying carbon dioxide in oil and gas reservoirs, the disclosure can also store hydrogen as a reactant and methane as a product in depleted oil and gas reservoirs, which can alleviate the problem of imbalance between energy supply and demand.

DESCRIPTION OF THE DRAWINGS

The FIGURE is a schematic diagram of a method for cyclic biochemical conversion of carbon dioxide and hot gas cogeneration in depleted oil and gas reservoirs according to the disclosure.

DESCRIPTION OF THE EMBODIMENTS

In order for persons skilled in the art to understand the technical solution of the disclosure clearly, the technical solution of the disclosure will be described in detail below with reference to specific embodiments.

Example 1

A method for cyclic biochemical conversion of carbon dioxide and hot gas cogeneration in depleted oil and gas reservoirs is provided, and a flow chart of the method is shown in the FIGURE, which specifically includes the following steps.

S1: depleted oil and gas reservoirs with an anticline or fault structure, a porosity greater than 10%, a permeability greater than 10 mD, a water saturation greater than 10%, a mineralization of the formation water less than 150 g/L with a pH value being in a range of 6.4 to 7.5 are selected as target oil and gas reservoirs, and biochemical conversion of carbon dioxide is carried out.

S2: the temperature of the target depleted oil and gas reservoir is calculated based on geothermal gradient theory or the temperature of the target depleted oil and gas reservoir is directly tested to determine whether the temperature is in a range of 30° C. to 70° C. If the temperature of the target depleted oil and gas reservoir is higher than 70° C., then cold water (fresh water of 5° C. to 20° C.) is cyclically injected into the target oil and gas reservoir to extract heat from the target depleted oil and gas reservoir (geothermal development) until the temperature of the reservoir drops to 30° C. to 70° C.

The formation water of the target depleted oil and gas reservoir is sampled using technical means such as enrichment culture, in-situ culture or, co-culture to determine the quantity of methanogenic archaea in the formation water. For details, reference may be made to the literature (DING Jijuan, LIU Fei, GU Hang, YU Xiaoli, HE Zhili. Isolation and culture of methanogenic and methanotrophic archaea: a review [J]. Microbiology China, 2022, 49(6): 2266-2280). The calculation is performed based on the weight of a single methanogenic archaeon being $1×10^{-12}$ g to determine whether the content of methanogenic archaea in the formation water is greater than $1×10^{-4}$ g/L. If the content of the methanogenic archaea is less than $1×10^{-4}$ g/L, then artificially cultured methanogenic archaea on the ground are injected into the target depleted oil and gas reservoir until the content is in a range of $1×10^{-4}$ g/L to $1×10^{-2}$ g/L, and then step S3 is proceeded. If the content of methanogenic archaea in the target depleted oil and gas reservoir is greater than or equal to $1×10^{-4}$ g/L, then step S3 is proceeded directly.

S3: a mixture of carbon dioxide and hydrogen is injected into the target depleted oil and gas reservoir through a gas injection well. The injection pressure of the gas injection well should be lower than the fracture pressure of the reservoir rock, and the ratio of carbon dioxide to hydrogen in the mixed gas is 3:13 to 3:12. The carbon dioxide is $CO_2$ captured from industrial waste gas, the atmosphere, or a mixture of the industrial waste gas and the atmosphere, and hydrogen is hydrogen produced by electrolysis of water, hydrogen produced from fossil energy, or hydrogen produced from industrial by-products.

S4: the gas injection well is shut down for half a year to one year to wait for the methanogenic archaea to convert the carbon dioxide and hydrogen in the target depleted oil and gas reservoir into methane, and heat energy is released. Under the action of methanogenic archaea, the thermal reaction equation for converting carbon dioxide and hydrogen into methane is as follows. Afterward, the methane and heat energy in the target depleted oil and gas reservoir are exploited.

In this disclosure, through capturing and transporting $CO_2$ in the atmosphere or industrial waste gas to the target depleted oil and gas reservoir, methane is finally converted under the action of methanogenic archaea. After being used by factories or users, methane generates $CO_2$ and is emitted into the atmosphere to be captured again, thereby realizing cyclic biochemical conversion of carbon dioxide and hot gas cogeneration in depleted oil and gas reservoirs, which is beneficial to the development of a carbon circular economy.

Example 2 is an application case of the method for cyclic biochemical conversion of carbon dioxide and hot gas cogeneration in depleted oil and gas reservoirs, which is as follows.

An anticlinal sandstone gas reservoir with a burial depth of 1000 m is selected as the target depleted oil and gas reservoir. The original pressure of the gas reservoir is 10 MPa. After production, the reservoir pressure has been depleted to 2 MPa. The porosity of the gas reservoir is 0.2, the permeability is 20 mD, the water saturation is 20%, and the pH value of the formation water of the gas reservoir is 6.5 and the mineralization is 100 g/L. The temperature of the reservoir of the gas reservoir is calculated to be 40° C. according to the geothermal gradient theory.

The formation water of the gas reservoir is sampled, and the content of methanogenic archaea in the formation water of the gas reservoir is determined to be 1×10-5 g/L by means of enrichment culture. In order to improve the efficiency of biochemical conversion of $CO_2$, cultured methanogenic archaea on the ground are injected into the gas reservoir before injecting $H_2$ and $CO_2$ into the gas reservoir so that the content reaches $1\times10^{-3}$ g/L. Then, under the condition that the wellhead pressure of the gas injection well is constant at 8 MPa, a mixture (hydrogen-containing industrial waste gas) of $H_2$ and $CO_2$ is injected into the gas reservoir at a volume ratio of 4:1 until the partial pressures of $H_2$ and $CO_2$ in the reservoir are 4 MPa and 1 MPa respectively.

After shutting down the well for 300 days, until the methanogenic archaea convert most of the $H_2$ and $CO_2$ into $CH_4$, the gas in the gas reservoir is extracted for gas chromatography analysis. The content of $CH_4$ has reached as high as 97.1%, and the $CO_2$ conversion ratio accounts for 98.3%. Moreover, the temperature of the reservoir is monitored to rise to 46° C. Then, the well is opened for production, and the extracted natural gas is directly exported and utilized. Since the reservoir temperature (30° C. to 70° C.) is still within the suitable temperature range for biochemical conversion, a cooling treatment is not needed for the reservoir, and a next stage of the cycle may be proceeded.

The embodiments are specific implementations of the disclosure, but the implementation of the disclosure is not limited by the embodiments. Any other combinations, changes, modifications, substitutions, and simplifications that do not exceed the design ideas of the disclosure fall within the scope of protection of the disclosure.

What is claimed is:

1. A method for cyclic biochemical conversion of carbon dioxide and hot gas cogeneration in a depleted oil and gas reservoir, comprising steps as follows:
    a step S1: selecting a depleted oil and gas reservoir suitable for the biochemical conversion of carbon dioxide as a target depleted oil and gas reservoir;
    a step S2: adjusting a temperature of the target depleted oil and gas reservoir to 30° C. to 70° C. and detecting whether formation water of the target depleted oil and gas reservoir contains methanogenic archaea, wherein in response to the target depleted oil and gas reservoir not containing the methanogenic archaea, injecting the methanogenic archaea into the target depleted oil and gas reservoir, and then performing a step S3, and in response to the target depleted oil and gas reservoir containing the methanogenic archaea, proceeding directly to the step S3;
    the step S3: injecting a mixture of carbon dioxide and hydrogen into the target depleted oil and gas reservoir through a gas injection well;
    step S4: shutting down the gas injection well for half a year to one year to wait for the methanogenic archaea to convert the carbon dioxide and hydrogen in the target depleted oil and gas reservoir into methane and exploiting methane and heat energy in the target depleted oil and gas reservoir;
    wherein:
    a structure of the target depleted oil and gas reservoir in the step S1 is an anticline or a fault with a porosity greater than 10%, a permeability greater than 10 mD, a water saturation greater than 10%, and a mineralization of the formation water less than 150 g/L with a pH value being in a range of 6.4 to 7.5; and
    a specific method of adjusting the temperature of the target depleted oil and gas reservoir to 30° C. to 70° C. in the step S2 comprises injecting pre-fluid into the target depleted oil and gas reservoir so that the temperature of the target depleted oil and gas reservoir drops to 30° C. to 70° C. in response to the temperature of the target depleted oil and gas reservoir being higher than 70° C.

2. The method of claim 1, wherein the pre-fluid is fresh water of 5° C. to 20° C.

3. The method of claim 2, wherein the methanogenic archaea in the step S2 is selected from one or more of methanobacteriaceae, *Methanothermus stetter*, *Methanococcus kluyer* and vam niel, methanogenus, and *Methanoplanus wildgruber*.

4. The method of claim 3, wherein a criterion for not containing the methanogenic archaea in the step S2 is that a content of the methanogenic archaea is less than $1\times10^{-4}$ g/L.

5. The method of claim 4, wherein in the step S3, a gas injection pressure of the gas injection well needs to satisfy that a bottom hole pressure is lower than a fracture pressure of a reservoir rock.

6. The method of claim 5, wherein a volume ratio of carbon dioxide to hydrogen in the step S3 is 3:13 to 3:12.

7. The method of claim 1, wherein methane and the heat energy exploited in the step S4 are directly exported to users and/or are exported to the users after power generation.

* * * * *